US012793135B2

(12) United States Patent
Crumb et al.

(10) Patent No.: US 12,793,135 B2
(45) Date of Patent: Nov. 10, 2026

(54) SYSTEM AND COMPUTER METHOD FOR TRADING A COMMODITY WITH CARRY COSTS

(71) Applicant: Abaxx Technologies Corp., Christ Church (BB)

(72) Inventors: Joshua Crumb, Christ Church (BB); Andrew Fedak, Christ Church (BB); Christopher A. Wiklof, Everett, WA (US)

(73) Assignee: ABAXX TECHNOLOGIES CORP., Christ Church (BB)

( * ) Notice: Subject to any disclaimer, the term of this patent is extended or adjusted under 35 U.S.C. 154(b) by 0 days.

(21) Appl. No.: 19/205,227

(22) Filed: May 12, 2025

(65) Prior Publication Data

US 2025/0278787 A1 Sep. 4, 2025

Related U.S. Application Data

(62) Division of application No. 16/703,726, filed on Dec. 4, 2019, now abandoned.

(Continued)

(51) Int. Cl.

*G06Q 40/04* (2012.01)
*A61K 49/00* (2006.01)

(Continued)

(52) U.S. Cl.

CPC ......... *G06Q 40/04* (2013.01); *A61K 49/0032* (2013.01); *C07D 311/30* (2013.01);

(Continued)

(58) Field of Classification Search

CPC ...... G06Q 40/04; G06Q 10/083; G06Q 10/10; G06Q 20/108; G06Q 20/3678; G06Q 20/3829; G06Q 20/42; G06Q 30/0206; G06Q 40/02; G06Q 2220/00; G06Q 20/02; A61K 49/0032; C07D 311/30; C07D 311/58; C07D 311/92; C07D 405/04; C07D 405/14; C07D 491/16; C07D 519/00; G06F 3/04817; G06F 3/0486; G06F 16/2379;

(Continued)

(56) References Cited

U.S. PATENT DOCUMENTS 11,170,128 B2 11/2021 Kurian
2006/0080208 A1 4/2006 Harrison (Continued)

FOREIGN PATENT DOCUMENTS

WO WO-2018020373 A1 * 2/2018 .......... G06Q 20/065

OTHER PUBLICATIONS

"BLIC: A Blockchain Protocol for Manufacturing and Supply Chain Management of ICs", Sumanta Bose, IEEE, Jul. 1, 2018 (Year: 2018).*

(Continued)

*Primary Examiner* — Duan Zhang
(74) *Attorney, Agent, or Firm* — PANITCH SCHWARZE BELISARIO & NADEL LLP

(57) ABSTRACT

A distributed ledger-based commodity trading method and graphical user interface (GUI) includes creating and using a smart contract that specifies variable or unknown carry costs, and covering actual carry costs with a reserve account of a cryptographic currency or cryptographic token.

20 Claims, 3 Drawing Sheets

Related U.S. Application Data

(60) Provisional application No. 62/775,778, filed on Dec. 5, 2018.

(51) Int. Cl.

| | |
|---|---|
| ***C07D 311/30*** | (2006.01) |
| ***C07D 311/58*** | (2006.01) |
| ***C07D 311/92*** | (2006.01) |
| ***C07D 405/04*** | (2006.01) |
| ***C07D 405/14*** | (2006.01) |
| ***C07D 491/16*** | (2006.01) |
| ***C07D 519/00*** | (2006.01) |
| ***G06F 3/04817*** | (2022.01) |
| ***G06F 3/0486*** | (2013.01) |
| ***G06F 16/23*** | (2019.01) |
| ***G06F 16/27*** | (2019.01) |
| ***G06F 21/60*** | (2013.01) |
| ***G06Q 10/083*** | (2023.01) |
| ***G06Q 10/10*** | (2023.01) |
| ***G06Q 20/10*** | (2012.01) |
| ***G06Q 20/36*** | (2012.01) |
| ***G06Q 20/38*** | (2012.01) |
| ***G06Q 20/42*** | (2012.01) |
| ***G06Q 30/0201*** | (2023.01) |
| ***G06Q 40/02*** | (2023.01) |
| ***G10L 15/26*** | (2006.01) |
| ***H04L 9/06*** | (2006.01) |
| ***H04L 9/08*** | (2006.01) |
| ***H04L 9/30*** | (2006.01) |
| ***H04L 51/046*** | (2022.01) |
| ***H04N 7/15*** | (2006.01) |
| *H04L 9/00* | (2022.01) |

(52) U.S. Cl.

CPC .......... *C07D 311/58* (2013.01); *C07D 311/92* (2013.01); *C07D 405/04* (2013.01); *C07D 405/14* (2013.01); *C07D 491/16* (2013.01); *C07D 519/00* (2013.01); *G06F 3/04817* (2013.01); *G06F 3/0486* (2013.01); *G06F 16/2379* (2019.01); *G06F 16/27* (2019.01); *G06F 21/602* (2013.01); *G06Q 10/083* (2013.01); *G06Q 10/10* (2013.01); *G06Q 20/108* (2013.01); *G06Q 20/3678* (2013.01); *G06Q 20/3829* (2013.01); *G06Q 20/42* (2013.01); *G06Q 30/0206* (2013.01); *G06Q 40/02* (2013.01); *G10L 15/26* (2013.01); *H04L 9/0637* (2013.01); *H04L 9/0643* (2013.01); *H04L 9/0894* (2013.01); *H04L 9/30* (2013.01); *H04L 51/046* (2013.01); *H04N 7/155* (2013.01); *G06Q 2220/00* (2013.01); *H04L 9/50* (2022.05)

(58) Field of Classification Search

CPC .... G06F 16/27; G06F 21/602; G06F 21/6254; G06F 21/64; G10L 15/26; H04L 9/0637; H04L 9/0643; H04L 9/0894; H04L 9/30; H04L 51/046; H04L 9/50; H04L 2209/56; H04L 9/3239; H04L 63/0421; H04L 63/0442; H04L 63/10; H04N 7/155

See application file for complete search history.

(56) References Cited

U.S. PATENT DOCUMENTS

| | | | |
|---|---|---|---|
| 2006/0235779 | A1 | 10/2006 | Drew et al. |
| 2009/0248563 | A1 | 10/2009 | Deasy et al. |
| 2011/0145030 | A1 | 6/2011 | Allen |
| 2011/0213694 | A1 | 9/2011 | Burns et al. |
| 2011/0258101 | A1 | 10/2011 | Albertelli et al. |
| 2012/0130923 | A1 | 5/2012 | Shah |
| 2013/0054405 | A1 | 2/2013 | Rabenold et al. |
| 2014/0297400 | A1 | 10/2014 | Sandholm |
| 2017/0351993 | A1* | 12/2017 | Vengalathur Srinath .................... G09F 3/00 |
| 2019/0354945 | A1 | 11/2019 | Mahajan et al. |
| 2020/0051011 | A1* | 2/2020 | Dasari ................... H04L 9/0637 |
| 2020/0184558 | A1 | 6/2020 | Crumb et al. |
| 2020/0184565 | A1 | 6/2020 | Crumb et al. |

OTHER PUBLICATIONS

Eskandari, Shayan et al, “On the feasibility of decentralized derivatives markets”, Feb. 14, 2018, 16 pages.

RFC 6750: OAuth 2.0 Bearer Token Usage, SmartBear, 2023, 14 pages.

Kumar, Rajesh, “What is Bearer token and How it works?”, DevOpsSchool.com, May 7, 2021, 8 pages.

* cited by examiner

SYSTEM AND COMPUTER METHOD FOR TRADING A COMMODITY WITH CARRY COSTS

CROSS-REFERENCE TO RELATED APPLICATIONS

The present application claims priority benefit from U.S. Provisional Patent Application No. 62/775,778, entitled "SYSTEM AND COMPUTER METHOD FOR TRADING A COMMODITY WITH CARRY COSTS," filed Dec. 5, 2018, which application, to the extent not inconsistent with the disclosure herein, is incorporated herein by reference.

SUMMARY

According to an embodiment, a computer method and graphical user interface (GUI) for executing a smart commodity contract includes displaying, on an electronic display of a user device, a GUI including an indication of a commodity contract for future delivery of a commodity at a nominal price, the nominal price including estimated carry costs, according to a smart contract carried by at least one non-transitory computer readable memory and accessed via a distributed ledger. The computer method and GUI for executing a smart commodity contract includes displaying, on the electronic display via the GUI, a payment field for receiving electronic payment for the future delivery of the commodity at the nominal price; and receiving, via the GUI, an entry corresponding to a link to a buyer account or wallet to operate as a source of the electronic payment. The computer method and GUI for executing a smart commodity contract includes transferring, from the buyer account or wallet into a server computer, the at least partial electronic payment for the future delivery of the commodity; and displaying, via the GUI, a reserve account balance in an amount specified by the smart contract, the reserve account balance including an apportionment for the estimated carry costs. The computer method and GUI for executing a smart commodity contract includes receiving, into the buyer account from the server computer, an electronic token representing the smart contract for future delivery of the commodity at a specified location for an actual but unknown price; displaying, in the GUI, information corresponding to receiving the electronic token; and receiving and displaying, in the GUI, cost data corresponding to an actual carry cost of handling the commodity. The computer method and GUI for executing a smart commodity contract includes displaying, in the GUI, a modified reserve account balance requirement; receiving an input, via the GUI from the buyer, of an agreement to transfer funds from or to the link to the source of the electronic payment corresponding to the modified reserve account balance requirement. The computer method and GUI for executing a smart commodity contract includes displaying, in the GUI, an acknowledgement of electronic payment receipt.

According to an embodiment, a computer method for executing a smart commodity contract includes receiving, from a buyer account into a server computer, at least partial electronic payment for future delivery of a commodity at a nominal price, according to a smart contract carried by at least one non-transitory computer readable memory. The smart contract specifies the nominal price including estimated carry costs corresponding to delivering the commodity. The computer method includes establishing, and displaying via a GUI, a reserve account balance in an amount specified by the smart contract. The reserve account balance includes an apportionment for the estimated carry costs. The computer method includes transferring, to the buyer account from the server computer, an electronic token representing the smart contract for future delivery of the commodity at a specified location for an actual but unknown price, and receiving cost data corresponding to an actual cost of handling the commodity. The computer method includes performing a new estimate of carry costs corresponding to handling the commodity, updating the smart contract to include the new estimate of the carry costs, modifying the reserve account balance requirement, and outputting data from the server computer to the buyer to inform the buyer of the modified reserve account balance requirement.

DETAILED DESCRIPTION

Figure 1:
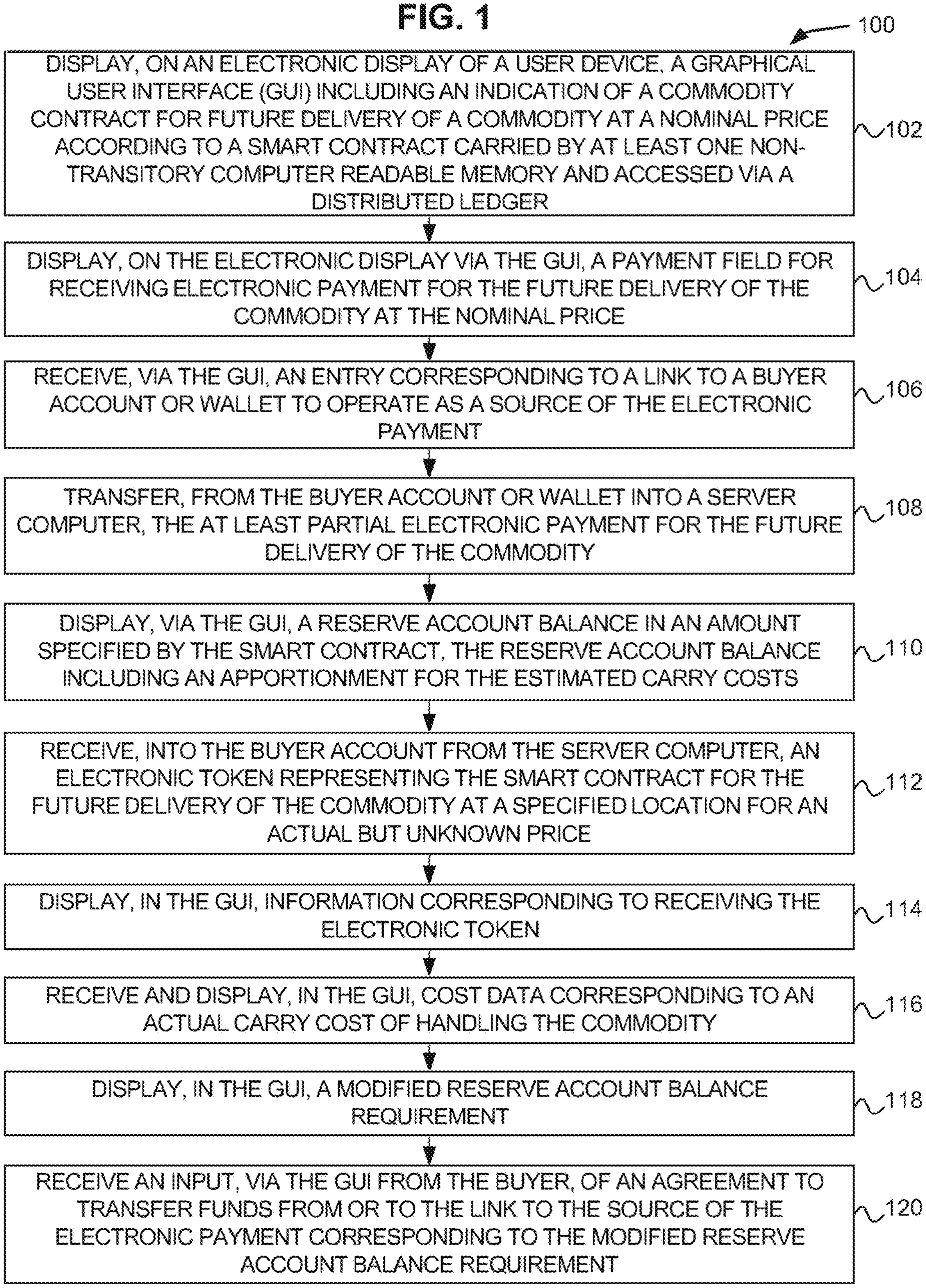
FIG. 1 is a flow chart of a computer method and graphical user interface (GUI) for executing a smart commodity contract, according to an embodiment.

In the following detailed description, reference is made to the accompanying drawings, which form a part hereof. In the drawings, similar symbols typically identify similar components, unless context dictates otherwise. Other embodiments may be used and/or other changes may be made without departing from the spirit or scope of the disclosure.

Figure 2:
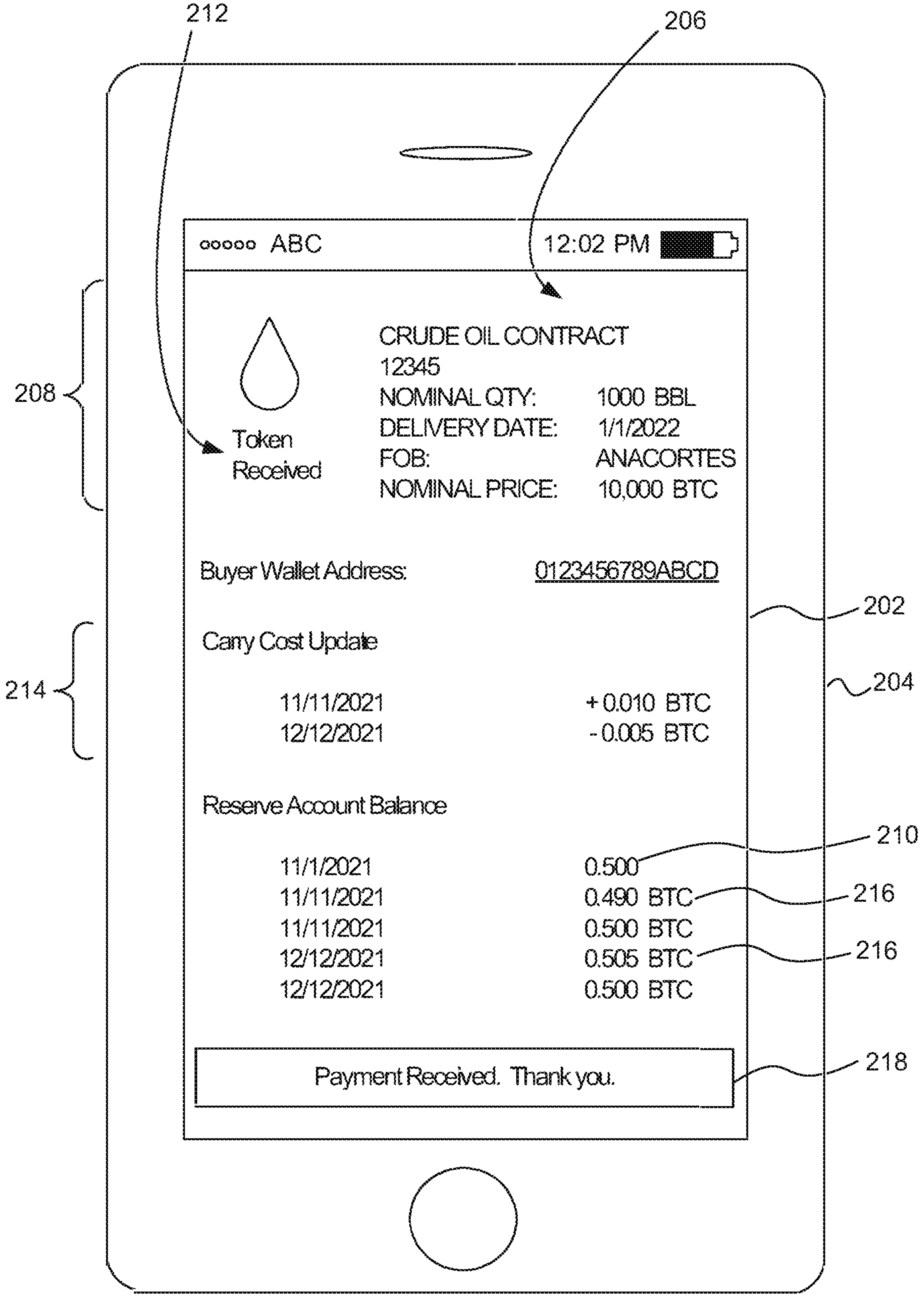
FIG. 2 is a diagram of the GUI for executing a smart commodity contract of FIG. 1, according to an embodiment.

FIG. 1 is a flow chart of a computer method 100 and graphical user interface (GUI) 206 for executing a smart commodity contract, according to an embodiment. FIG. 2 is a diagram of the GUI 206 for executing a smart commodity contract of FIG. 1, according to an embodiment.

According to an embodiment, referring to FIGS. 1 and 2, a computer method and graphical user interface (GUI) 100 for executing a smart commodity contract includes, in step 102, displaying, on an electronic display 202 of a user device 204, a GUI 206 including an indication 208 of a commodity contract for future delivery of a commodity at a nominal price, the nominal price including estimated carry costs, according to a smart contract carried by at least one non-transitory computer readable memory and accessed via a distributed ledger. Step 104 includes displaying, on the electronic display 202 via the GUI 206, a payment field (not shown) for receiving electronic payment for the future delivery of the commodity at the nominal price. Step 106 includes receiving, via the GUI 206, an entry corresponding to a link to a buyer account or wallet to operate as a source of the electronic payment. Step 108 includes transferring, from the buyer account or wallet into a server computer, the at least partial electronic payment for the future delivery of the commodity. Step 110 includes displaying, via the GUI 206, a reserve account balance 210 in an amount specified by the smart contract, the reserve account balance 210 including an apportionment for the estimated carry costs. Step 112 includes receiving, into the buyer account from the server computer, an electronic token representing the smart contract for future delivery of the commodity at a specified location for an actual but unknown price. Step 114 includes displaying, in the GUI 206, information 212 corresponding to receiving the electronic token in step 112. Step 116 includes receiving and displaying, in the GUI 206, cost data 214 corresponding to an actual carry cost of handling the commodity. Step 118 includes displaying, in the GUI 206, a modified reserve account balance requirement 216. Step 120 includes receiving an input, via the GUI 206 from the buyer, of an agreement to transfer funds from or to the link to the source of the electronic payment corresponding to the modified reserve account balance requirement 216. The computer method 100 and the GUI 206 for executing a smart commodity contract includes displaying, in the GUI 206, an acknowledgement 218 of electronic payment receipt.

According to an embodiment, the commodity includes a physical commodity. According to an embodiment, the carry costs include a physical commodity transportation cost. In one embodiment, the carry costs include a physical commodity storage cost. In another embodiment, the carry costs include a physical commodity quantity reduction related to loss to evaporation, sublimation, leakage, spillage, compression, temperature change, or chemical reaction (such as oxidation).

According to an embodiment, the computer method 100 and GUI 206 for executing a smart commodity contract may further include (not shown) receiving and displaying, in the GUI 206 from the server computer, a new estimate of carry costs corresponding to handling the commodity. According to an embodiment, the computer method 100 and GUI 206 for executing a smart commodity contract may further include (not illustrated) displaying, in the GUI 206, information regarding updating the smart contract to include the new estimate of the carry costs. In an embodiment, receiving the new estimate of carry costs includes receiving an update of the prior estimate to include actual carry costs.

According to an embodiment, the computer method 100 and GUI 206 for executing a smart commodity contract further include establishing and displaying, via the GUI 206, information corresponding to the reserve account balance 210 in an amount specified by the smart contract including an apportionment for the new estimated carry costs in step 110.

According to an embodiment, the establishing and displaying, via the GUI 206, of the information corresponding to establishing the reserve account balance 210, in step 110, includes (not separately illustrated) displaying a notice of automatic transferring of electronic funds to or from the reserve account. The receiving of the input, via the GUI 206 from the buyer, of the agreement to transfer the funds from or to the link to the source of the at least partial electronic payment, in step 120, may include receiving a pre-authorization agreement or acknowledgement at a time prior to the transfer.

According to an embodiment, establishing and displaying, via the GUI 206, the reserve account balance 210, in step 110, includes (not separately illustrated) receiving a transfer of electronic funds from the buyer wallet into the server computer. According to another embodiment, establishing and displaying, via the GUI 206, the reserve account balance 210, in step 110, includes (not separately illustrated) receiving an electronic withdrawal of funds from the buyer wallet, and transferring the withdrawn funds to a buyer trust account as a blockchain currency transaction.

According to an embodiment, the computer method 100 and GUI 206 for executing a smart commodity contract further performing, with the server computer, an initial estimate of carry costs corresponding to carrying the commodity. In an embodiment, performing the initial estimate of carry costs corresponding to carrying the commodity includes performing an initial estimate of carry costs corresponding to at least one of handling, storing, analyzing, certifying, exchanging, swapping, capitalizing, franchising, optioning, delivering, sublimating, melting, freezing, cooling, heating, hardening, boiling, transporting, pumping, producing, injecting, evacuating, spewing, and showing a physical commodity.

According to an embodiment, the smart contract is carried by a distributed ledger carried by a plurality of non-transitory computer readable media. The distributed ledger may include a blockchain. In an embodiment, the blockchain includes a public blockchain. In another embodiment, the blockchain includes a private blockchain. Additionally and/or alternatively, the blockchain includes a permissioned blockchain.

According to an alternate embodiment, the smart contract is added to the distributed ledger as a transaction. In an embodiment, adding the smart contract to the distributed ledger includes encrypting the smart contract. In another embodiment, adding the smart contract to the distributed ledger includes storing the smart contract at one or more cloud locations, encrypting the one or more cloud locations, and entering the encrypted one or more cloud locations onto the distributed ledger as a transaction.

Figure 3:
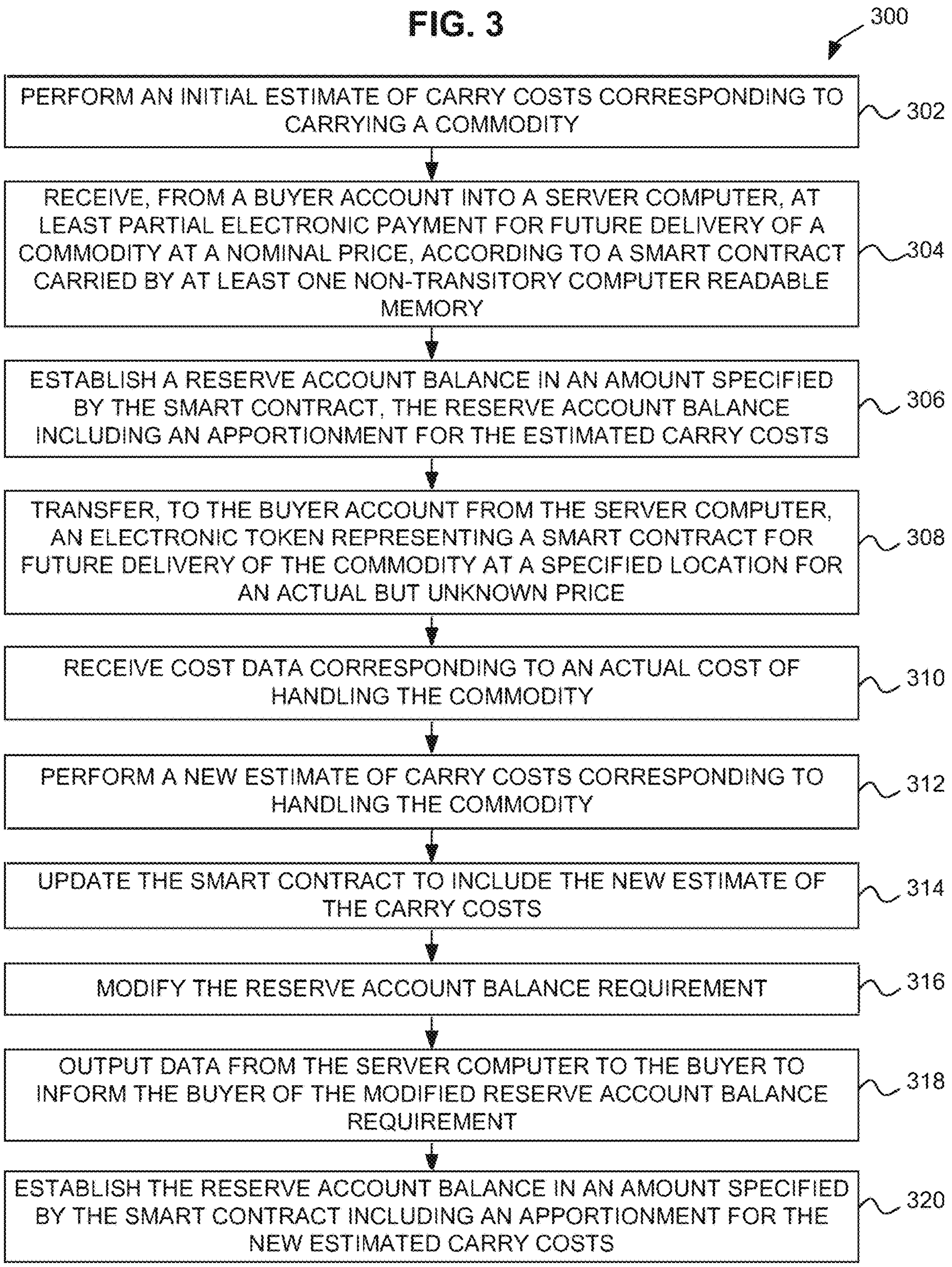
FIG. 3 is a flow chart of a computer method for executing a smart commodity contract, according to an embodiment.

FIG. 3 is a flow chart of a computer method 300 for executing a smart commodity contract, according to an embodiment.

According to an embodiment, the computer method 300 for executing a smart commodity contract includes, in step 304, receiving, from a buyer account into a server computer, at least partial electronic payment for future delivery of a commodity at a nominal price, according to a smart contract carried by at least one non-transitory computer readable memory. In an embodiment, the smart contract specifies the nominal price including estimated carry costs corresponding to delivering the commodity. For example, delivering the commodity may include handling, storing, analyzing, certifying, exchanging, swapping, capitalizing, franchising, optioning, delivering, sublimating, melting, freezing, cooling, heating, hardening, boiling, transporting, pumping, producing, injecting, evacuating, spewing, or showing a physical commodity. Step 306 includes establishing a reserve account balance in an amount specified by the smart contract, the reserve account balance including an apportionment for the estimated carry costs. Step 308 includes transferring, to the buyer account from the server computer, an electronic token representing the smart contract for future delivery of the commodity at a specified location for an actual but unknown price. Step 310 includes receiving cost data corresponding to an actual cost of handling the commodity. Step 312 includes performing a new estimate of carry costs (e.g., and/or revising the estimated carry costs) corresponding to handling the commodity. Step 314 includes updating the smart contract to include the new estimate of the carry costs. Step 316 includes modifying the reserve account balance requirement. Step 318 includes outputting data from the server computer to the buyer to inform the buyer of the modified reserve account balance requirement.

According to an embodiment, the commodity may include a physical commodity.

According to an embodiment, in step 312, performing a new estimate of carry costs includes updating the prior estimate to include actual carry costs.

According to an embodiment, the computer method 300 further includes, in step 320, establishing the reserve account balance in an amount specified by the smart contract including an apportionment for the new estimated carry costs. In one embodiment, establishing the reserve account balance includes automatically transferring electronic funds to or from the reserve account. In another embodiment, establishing the reserve account balance includes receiving a transfer of electronic funds from the buyer into the server computer. In another embodiment, establishing the reserve account balance includes receiving an electronic withdrawal of funds from the buyer, and transferring the withdrawn funds to a buyer account as a blockchain currency transaction. In another embodiment, establishing the reserve account balance includes issuing or receiving a transaction including a transfer of a distributed ledger hold value as a contractual encumbrance on a balance held at a specified exchange address. In another embodiment, establishing the reserve account balance includes establishing a reserve account balance including an apportionment for the estimated carry costs.

According to an embodiment, the computer method 300 further includes, in step 302, performing an initial estimate of carry costs corresponding to carrying the commodity. In an embodiment, performing the initial estimate of carry costs corresponding to carrying the commodity includes estimating carry costs corresponding to carry costs of a physical commodity. In another embodiment, performing an initial estimate of carry costs corresponding to carrying the commodity includes performing an initial estimate of carry costs corresponding to processing a physical commodity. In another embodiment, performing an initial estimate of carry costs corresponding to carrying the commodity includes performing an initial estimate of carry costs corresponding to at least one of handling, storing, analyzing, certifying, exchanging, swapping, capitalizing, franchising, optioning, delivering, sublimating, melting, freezing, cooling, heating, hardening, boiling, transporting, pumping, producing, injecting, evacuating, spewing, and showing a physical commodity.

According to an embodiment, in step 304, receiving, from the buyer account into the server computer, at least partial electronic payment for future delivery of the commodity at the nominal price according to the smart contract includes receiving a distributed ledger source address, an amount transferred, and a distributed ledger transfer history or transfer histories of the amount transferred. In an embodiment, receiving, from the buyer account into the server computer, at least partial electronic payment for future delivery of the commodity at the nominal price according to the smart contract further includes receiving a public key and a defined but anonymous identity associated with the distributed ledger transfer history. In an embodiment, receiving the public key and the known but anonymous identity associated with the distributed ledger transfer history further includes reporting aggregate transactions to/for each anonymous identity in a plurality of anonymous identities.

According to an embodiment, in step 304, receiving, from the buyer account into the server computer, at least partial electronic payment for future delivery of the commodity at the nominal price according to the smart contract includes receiving at least partial electronic payment for future delivery of a physical commodity at the nominal price according to a smart contract carried by a distributed ledger.

According to an embodiment, the nominal price includes estimated carry costs corresponding to carry costs of a physical commodity.

According to an embodiment, in step 308, transferring, to the buyer account from the server computer, an electronic token representing a smart contract for future delivery of the commodity at a specified location for an actual but unknown price includes transferring, to the buyer account from the server computer, an electronic bearer token representing a smart contract for future delivery of a physical commodity at a specified location for an actual but unknown price.

According to an embodiment, in step 312, performing a new estimate of carry costs corresponding to handling the commodity includes revising the estimated total carry costs to include changes in market pricing of the carry costs.

According to an embodiment, the smart contract is carried by a distributed ledger carried by a plurality of non-transitory computer readable media. In an embodiment, the distributed ledger includes a blockchain. In one embodiment, the blockchain includes a public blockchain. In another embodiment, the blockchain includes a private blockchain. In another embodiment, the blockchain includes a permissioned blockchain. In an embodiment, the smart contract is added to the distributed ledger as a transaction. In one embodiment, adding the smart contract to the distributed ledger includes encrypting the smart contract. In another embodiment, adding the smart contract to the distributed ledger includes storing the smart contract at one or more cloud locations, encrypting the one or more cloud locations, and entering the encrypted one or more cloud locations onto the distributed ledger as a transaction.

While various aspects and embodiments have been disclosed herein, other aspects and embodiments are contemplated. The various aspects and embodiments disclosed herein are for purposes of illustration and are not intended to be limiting, with the true scope and spirit being indicated by the following claims.

What is claimed is:

1. A computer method for executing a smart commodity contract, comprising:

storing a smart contract on at least one non-transitory computer readable memory accessible via a distributed ledger;

executing the smart contract to determine a nominal price for future delivery of a commodity, the nominal price including estimated carry costs;

displaying, on an electronic display of a user device, a graphical user interface (GUI) including an indication of a commodity contract for future delivery of a commodity at a nominal price;

displaying, on the electronic display via the GUI, a payment field for receiving electronic payment for the future delivery of the commodity at the nominal price;

receiving, via the GUI, an entry corresponding to a link to a buyer account or wallet to operate as a source of the electronic payment;

transferring, from the buyer account or wallet into a server computer, the at least partial electronic payment for the future delivery of the commodity;

executing the smart contract to determine a reserve account balance, the reserve account balance including an apportionment for the estimated carry costs;

displaying, via the GUI, a reserve account balance;

transferring, by the server computer to the buyer account, an electronic token representing the smart contract for future delivery of the commodity at a specified location for an actual but unknown price, the electronic token being issued in accordance with the smart contract;

receiving, into the buyer account from the server computer, the electronic token;

displaying, in the GUI, information corresponding to receiving the electronic token;

receiving and displaying, in the GUI, cost data corresponding to an actual carry cost of handling the commodity;

determining a new estimate of carry costs corresponding to handling the commodity based at least in part on the cost data;

updating the smart contract with the new estimate of carry costs;

executing the smart contract to determine a modified reserve account balance requirement based at least in part on the cost data and the new estimate of carry costs;

displaying, in the GUI, the modified reserve account balance requirement; and receiving an input, via the GUI from the buyer, of an agreement to transfer funds from or to the link to the source of the electronic payment corresponding to the modified reserve account balance requirement.

2. The computer method for executing a smart commodity contract of claim 1, wherein the commodity comprises a physical commodity.

3. The computer method for executing a smart commodity contract of claim 2, wherein the carry costs include a physical commodity transportation cost.

4. The computer method for executing a smart commodity contract of claim 2, wherein the carry costs include a physical commodity storage cost.

5. The computer method for executing a smart commodity contract of claim 2, wherein the carry costs include a physical commodity quantity reduction related to loss to evaporation, sublimation, leakage, spillage, compression, temperature change, or chemical reaction.

6. The computer method for executing a smart commodity contract of claim 1, further comprising receiving and displaying, in the GUI from the server computer, the new estimate of carry costs corresponding to handling the commodity.

7. The computer method for executing a smart commodity contract of claim 6, further comprising displaying, in the GUI, information regarding the updating the smart contract to include the new estimate of the carry costs.

8. The computer method for executing a smart commodity contract of claim 6, wherein receiving the new estimate of carry costs includes receiving an update of the prior estimate to include actual carry costs.

9. The computer method for executing a smart commodity contract of claim 1, further comprising:

establishing, and displaying via the GUI, information corresponding to the reserve account balance in an amount specified by the smart contract including an apportionment for the new estimated carry costs.

10. The computer method for executing a smart commodity contract of claim 9, wherein establishing and displaying, via the GUI, information corresponding to the reserve account balance comprises:

displaying a notice of automatic transferring of electronic funds to or from the reserve account; and wherein receiving the input, via the GUI from the buyer, of the agreement to transfer the funds from or to the link to the source of the at least partial electronic payment includes receiving a pre-authorization agreement or acknowledgement at a time prior to the transfer.

11. The computer method for executing a smart commodity contract of claim 9, wherein establishing and displaying, via the GUI, information corresponding to the reserve account balance comprises:

receiving a transfer of electronic funds from the buyer wallet into the server computer.

12. The computer method for executing a smart commodity contract of claim 9, wherein establishing and displaying, via the GUI, information corresponding to the reserve account balance comprises:

receiving an electronic withdrawal of funds from the buyer wallet; and transferring the withdrawn funds to a buyer trust account as a blockchain currency transaction.

13. The computer method for executing a smart commodity contract of claim 1, wherein performing the initial estimate of carry costs corresponding to carrying the commodity comprises: performing an initial estimate of carry costs corresponding to at least one of handling, storing, analyzing, certifying, exchanging, swapping, capitalizing, franchising, optioning, delivering, sublimating, melting, freezing, cooling, heating, hardening, boiling, transporting, pumping, producing, injecting, evacuating, spewing, and showing a physical commodity.

14. The computer method for executing a smart commodity contract of claim 1, wherein the distributed ledger comprises a blockchain.

15. The computer method for executing a smart commodity contract of claim 14, wherein the blockchain comprises a public blockchain.

16. The computer method for executing a smart commodity contract of claim 14, wherein the blockchain comprises a private blockchain.

17. The computer method for executing a smart commodity contract of claim 14, wherein the blockchain comprises a permissioned blockchain.

18. The computer method for executing a smart commodity contract of claim 1, wherein the smart contract is added to the distributed ledger as a transaction.

19. The computer method for executing a smart commodity contract of claim 18, wherein adding the smart contract to the distributed ledger comprises encrypting the smart contract.

20. The computer method for executing a smart commodity contract of claim 18, wherein adding the smart contract to the distributed ledger comprises:

storing the smart contract at one or more cloud locations;

encrypting the one or more cloud locations; and entering the encrypted one or more cloud locations onto the distributed ledger as a transaction.

* * * * *